US00PP33534P3

(12) United States Plant Patent
Arpaia et al.

(10) Patent No.: US PP33,534 P3
(45) Date of Patent: Oct. 5, 2021

(54) AVOCADO TREE NAMED 'BL 5-552'

(50) Latin Name: ***Persea americana* Mill.**
Varietal Denomination: BL 5-552

(71) Applicant: The Regents of the University of California, Oakland, CA (US)

(72) Inventors: Mary Lu Arpaia, Visalia, CA (US); Eric Focht, Moreno Valley, CA (US); Gray E. Martin, Fallbrook, CA (US); Berthold O. Bergh, Riverside, CA (US)

(73) Assignee: The Regents of the University of California, Oakland, CA (US)

( * ) Notice: Subject to any disclaimer, the term of this patent is extended or adjusted under 35 U.S.C. 154(b) by 234 days.

(21) Appl. No.: 15/932,119

(22) Filed: Feb. 6, 2018

(65) Prior Publication Data

US 2019/0246537 P1 Aug. 8, 2019

(51) Int. Cl.
*A01H 5/08* (2018.01)
*A01H 6/52* (2018.01)

(52) U.S. Cl.
USPC ..... Plt./200
CPC ..... *A01H 6/525* (2018.05)

(58) Field of Classification Search
USPC ..... Plt./200
CPC ..... A01H 5/08
See application file for complete search history.

(56) References Cited

PUBLICATIONS https://www.myavocadotrees.com/proceedings-of-the-world-avocado-congress-iii-1995-114---118.html; 1995; 3 pages.*
https://www.myavocadotrees.com/proceedings-of-the-world-avocado-congress-iii-1995-114---118.html; 1995; 2 pages.*
Excerpt from Government Gazette South Africa, vol. 656, No. 43015, Feb. 14, 2020, 2 pages.
Excerpt from South Africa Government Notices, No. 1188, Nov. 2, 2018, 2 pages.
Application for a Plant Breeder's Right, No. PT 8557 for BL 555-2, Grant No. 20196973, submitted to South Africa PBR Office on Jun. 14, 2018, 5 pages.
Redacted Agreement for the variety known as "BL 555-2" or "555-2", executed on Jun. 5, 2015, 30 pages.
Redacted Test Agreement for the variety known as "BL 555-2" or "555-2", executed on Mar. 9, 1998, 3 pages.
Redacted Amendment to Test Agreement for the variety known as "BL 555-2" or "555-2", executed on May 27, 2008 and Jul. 14, 2008, 2 pages.

* cited by examiner

*Primary Examiner* — Kent L Bell
(74) *Attorney, Agent, or Firm* — Kilpatrick Townsend & Stockton LLP

(57) ABSTRACT

'BL 5-552' is a new and distinct variety of *Persea americana* tree. The variety exhibits an open, upright habit. The fruit is rhomboidal, or occasionally, obovate or high spheroid shaped, lacks shoulders, is generally green skinned, is distributed throughout the canopy and commonly is larger size than that of the 'Hass' variety. The leaves are displayed in a similar quantity to 'Hass' and are similar in shape to those of the 'Lamb/Hass' variety. 'BL 5-552' has moderate resistance to *Persea* mites. The variety is suitable for the production of quality avocado crop under commercial growing conditions.

7 Drawing Sheets

Genus and species: The avocado cultivar of this invention is botanically identified as *Persea americana* Mill.

Variety denomination: The variety denomination is 'BL 5-552'.

BACKGROUND OF THE INVENTION

The invention relates to a new and distinct plant variety of avocado tree named 'BL 5-552'. The new avocado variety is the product of a breeding program for new avocado varieties.

The seed that produced 'BL 5-552' was collected in 1984 from open pollinated 'Gwen' (U.S. Plant Pat. No. 5,298) avocado plants. The exact pollen parent is unknown. Seeds were planted in a test planting area to produce avocado seedlings in the spring of 1986. A single plant of 'BL 5-552' was selected with initial evaluation occurring in December 1991. 'BL 5-552' was first top-worked by grafting onto *Persea americana* seedlings in the spring of 1992 by the applicant in Riverside, Calif. The first fruit from the trees was tested in August 1994. This and subsequent asexual propagation confirmed that the new variety is stable and the progeny remain true to type.

BRIEF SUMMARY OF THE INVENTION

'BL 5-552' exhibit the following characteristics compared to other known varieties:

(a) Exhibits an open, upright growth habit with spreading branches that are more similar to 'N4(-)5' (variety denomination 'Harvest', U.S. Plant Pat. No. 14,238) than to 'BL 516' (unpatented).

(b) Forms rhomboidal, or occasionally, obovate or high spheroid shaped, generally green-skinned, fruit that is well-distributed around the tree and that lacks shoulders, commonly is larger than that of the 'Hass' variety, and matures slightly later then the fruit of the 'Hass' variety; and has yellow-green flesh of excellent eating quality that is free of obvious fibers;

(c) Forms leaves in lesser quantity than the 'BL 516' and 'Lamb/Hass' variety, and (d) Displays moderate resistance to the *Persea* mite.

'BL 5-552' can be distinguished from all previously known avocado varieties including the 'Hass' variety, the 'Gwen' variety, the 'Sir Prize' variety (U.S. Plant Pat. No. 9,709), the 'Lamb/Hass' variety (U.S. Plant Pat. No. 9,573), the 'N4(-)5' variety, the 'BL 516' variety and the '3-29-5' variety (U.S. Plant Pat. No. 14,239) in view of its distinctive combination of characteristics.

'BL 5-552' is believed to be well suited for the production of quality avocados under commercial growing conditions.

BRIEF DESCRIPTION OF THE PHOTOGRAPHS

The accompanying photographs illustrate the appearance of the new avocado tree and fruit. The color of the photographs might vary slightly compared to the variety description, however the botanical description are the most accurately description of the true color of this new variety.

FIG. 1A. FIG. 1B, FIG. 1C, and FIG. 1D four typical young 'BL 5-552' trees growing in South Africa of between 2 and 5 years of age.

DETAILED BOTANICAL DESCRIPTION

Figure 1A:
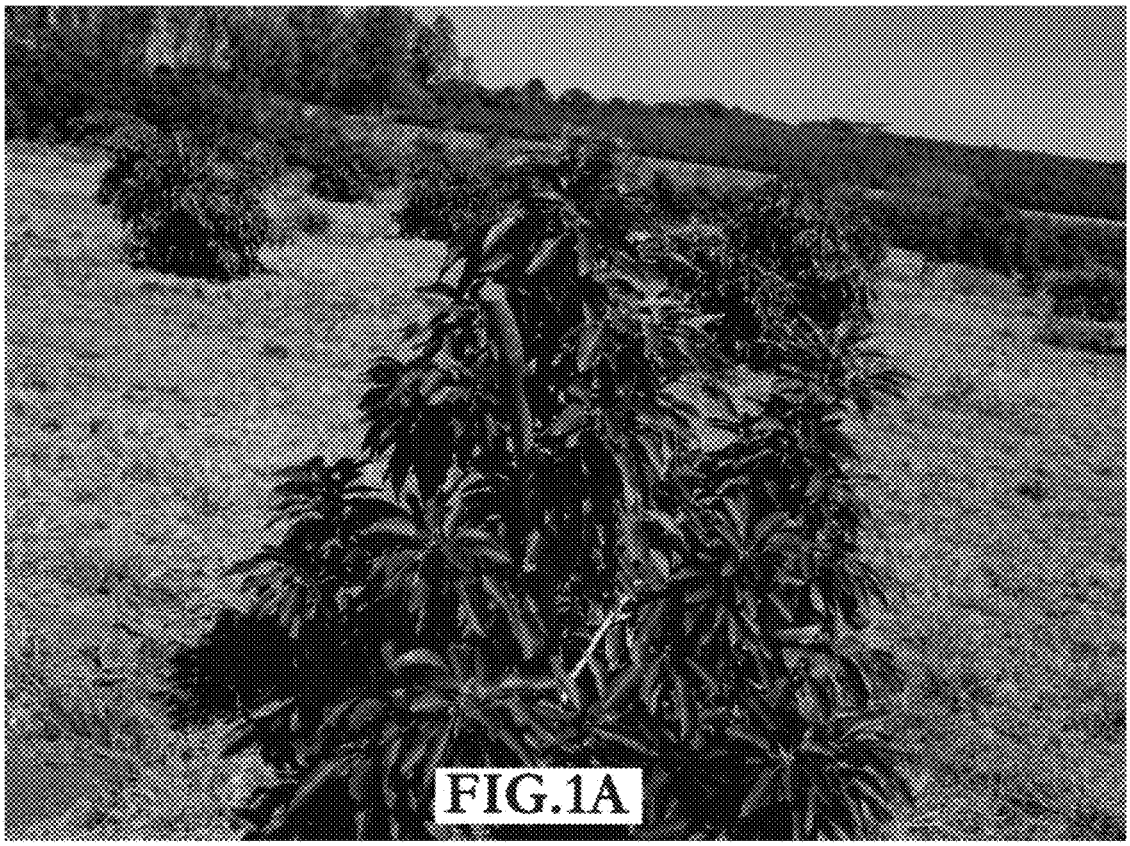
Figure 1B:
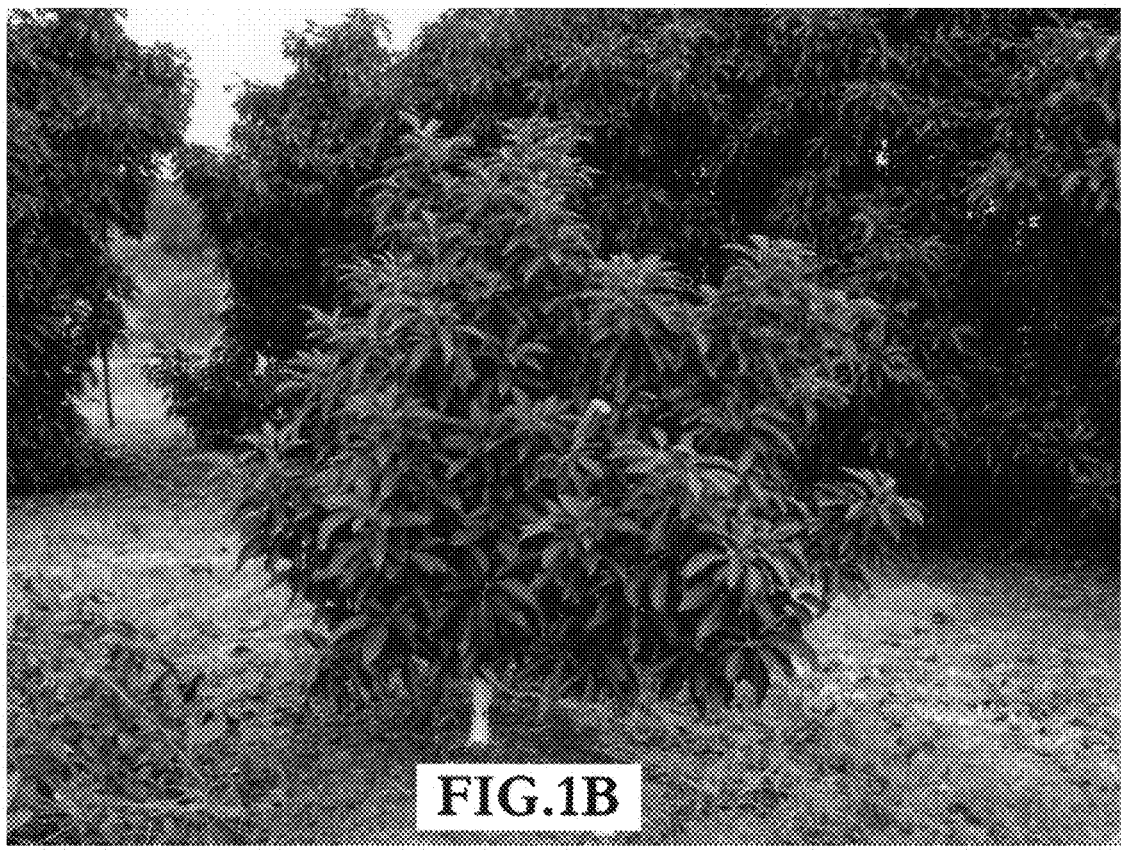
Figure 1C:
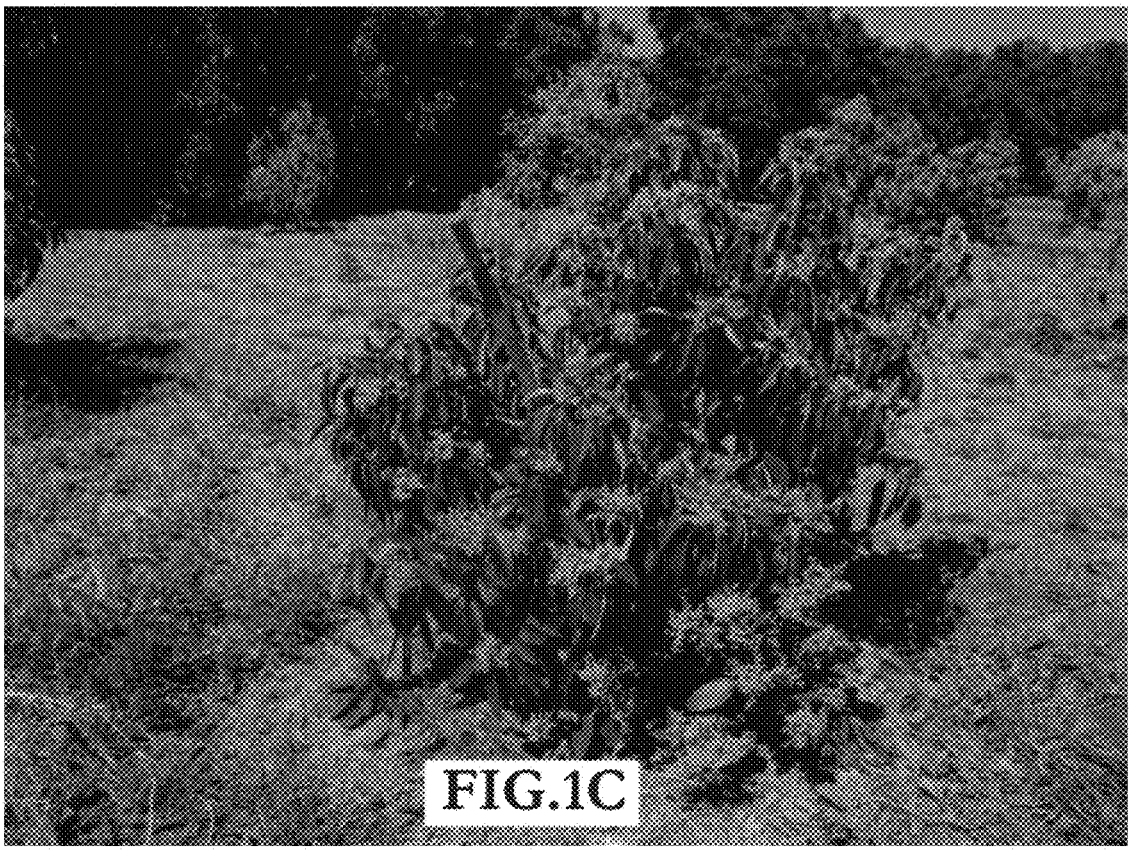
Figure 1D:
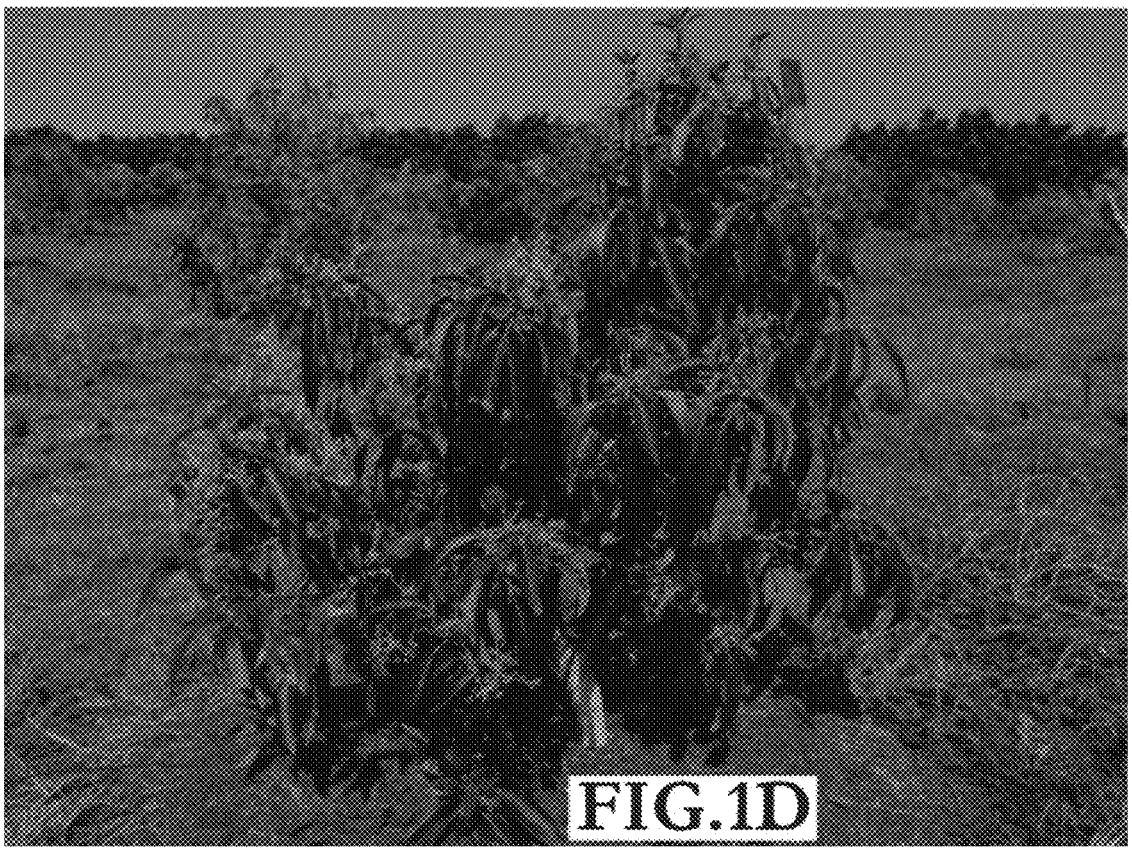
Figure 2A:
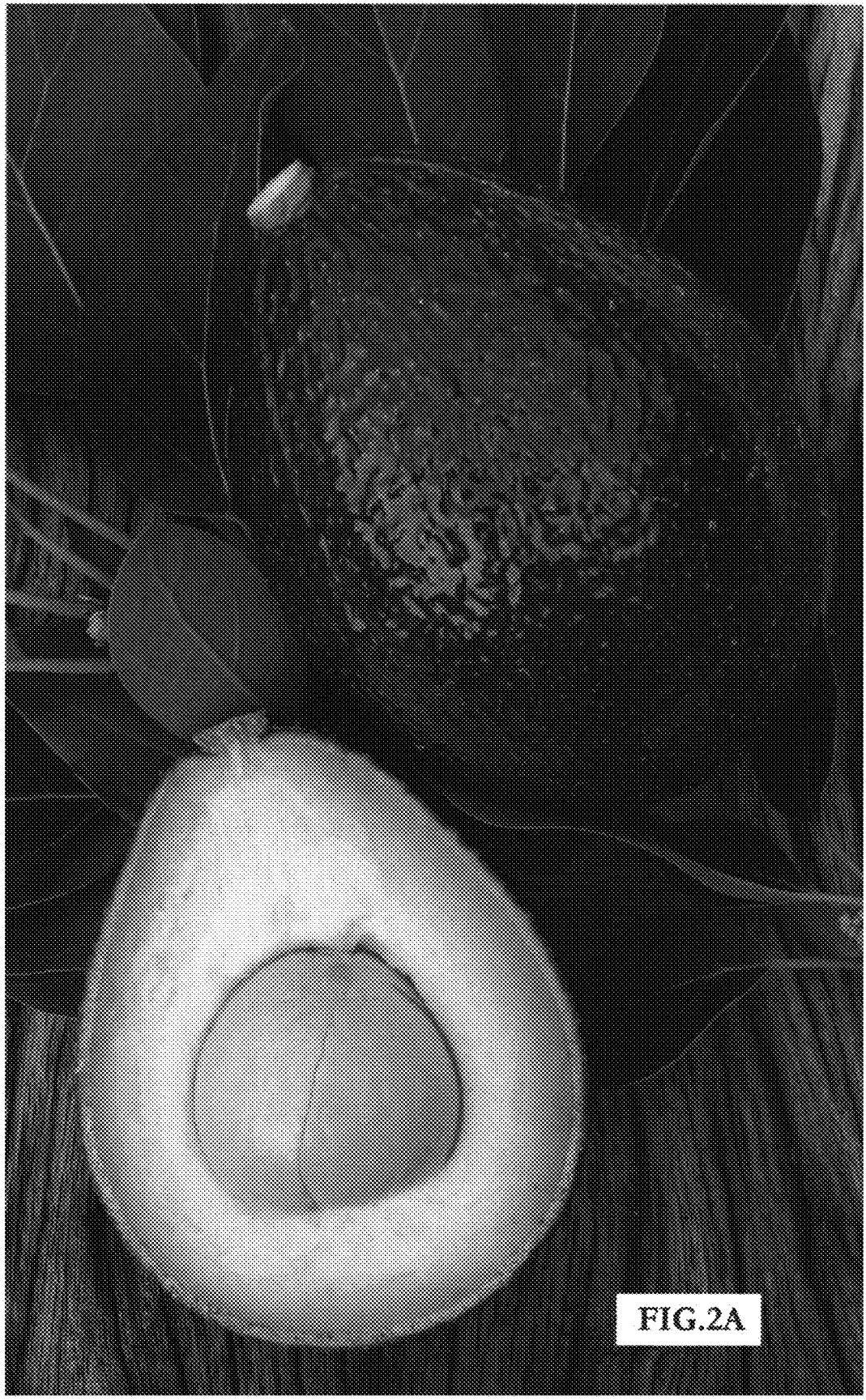
FIG. 2A and FIG. 2B illustrate typical external and internal ripe fruit of 'BL 5-552' obtained from trees grown in South Africa.
Figure 2B:
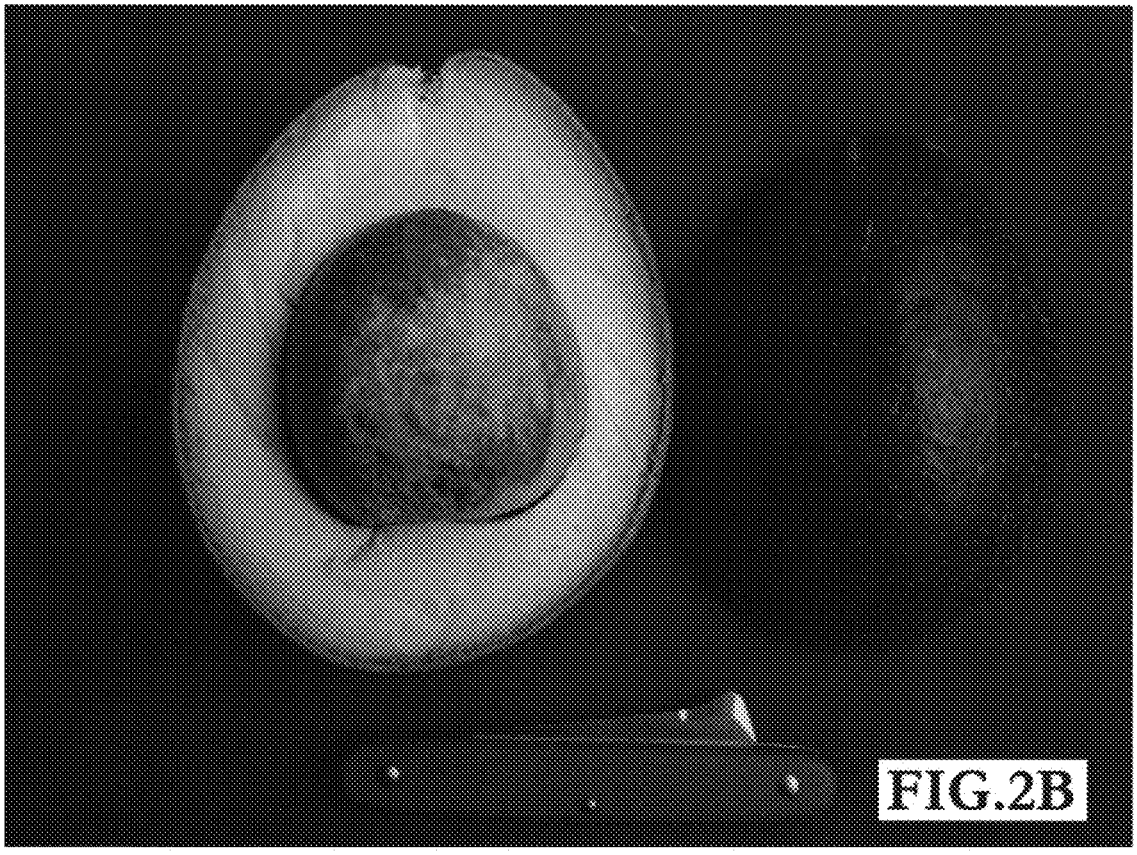
Figure 2C:
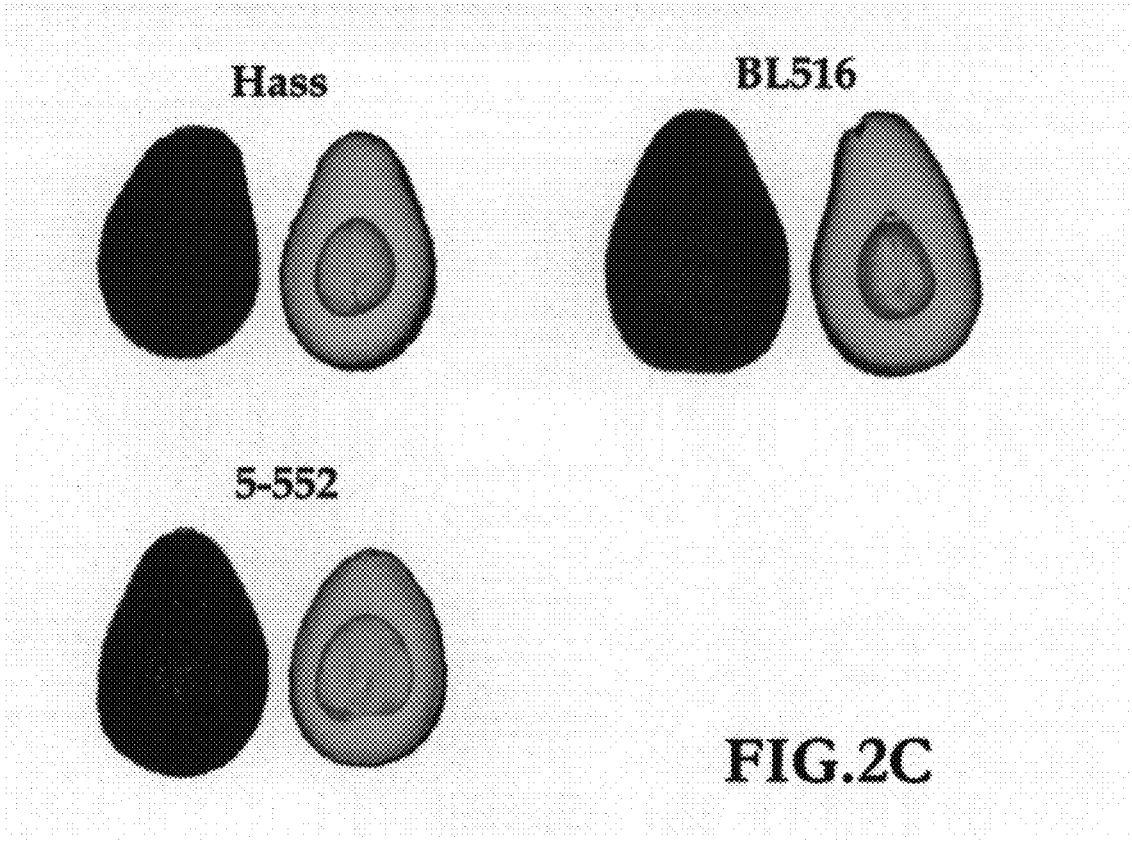
FIG. 2C illustrates typical external and internal 'BL 5-552' as contrasted to external and internal fruit of 'Hass' and 'BL 516' varieties as they appear in Southern California.
Figure 3A:
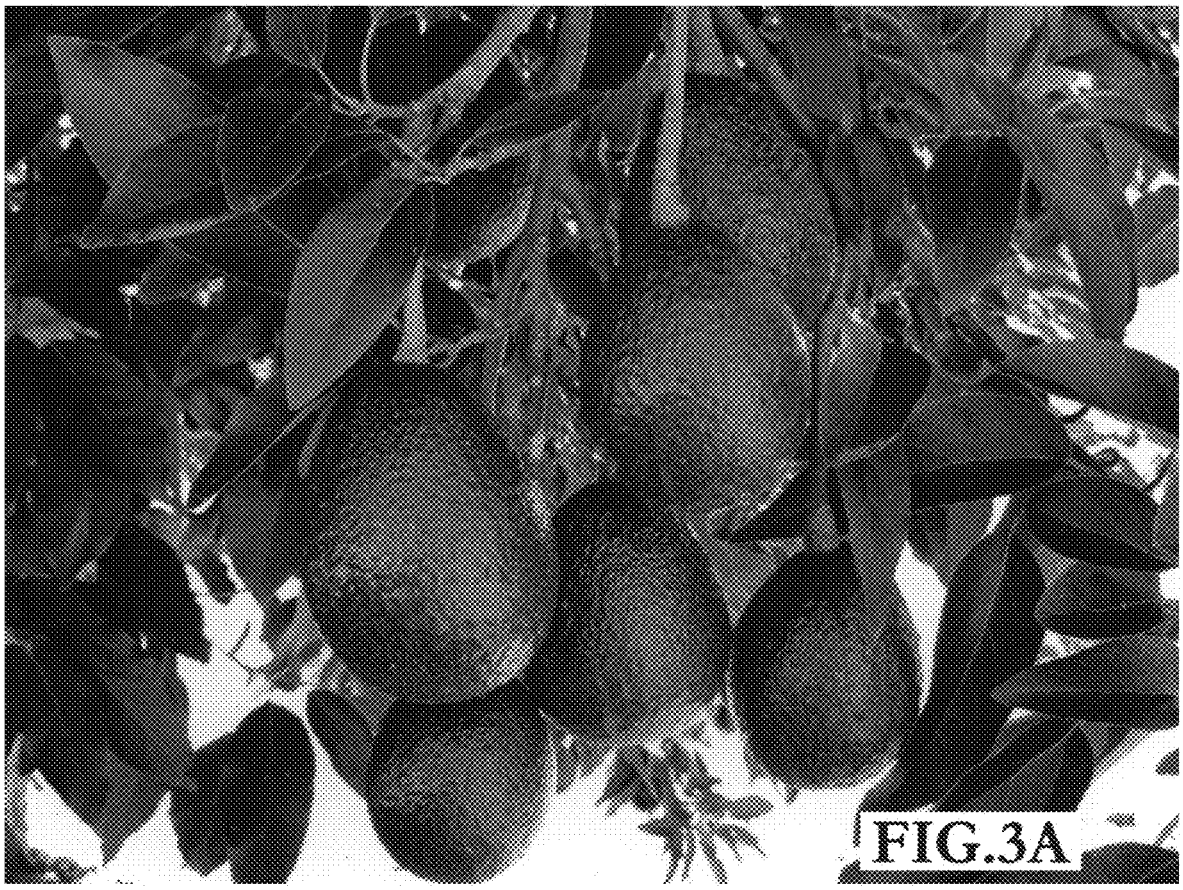
FIG. 3A and FIG. 3B illustrate typical bearing and appearance of 'BL 5-552' fruit hanging on the tree.
Figure 3B:
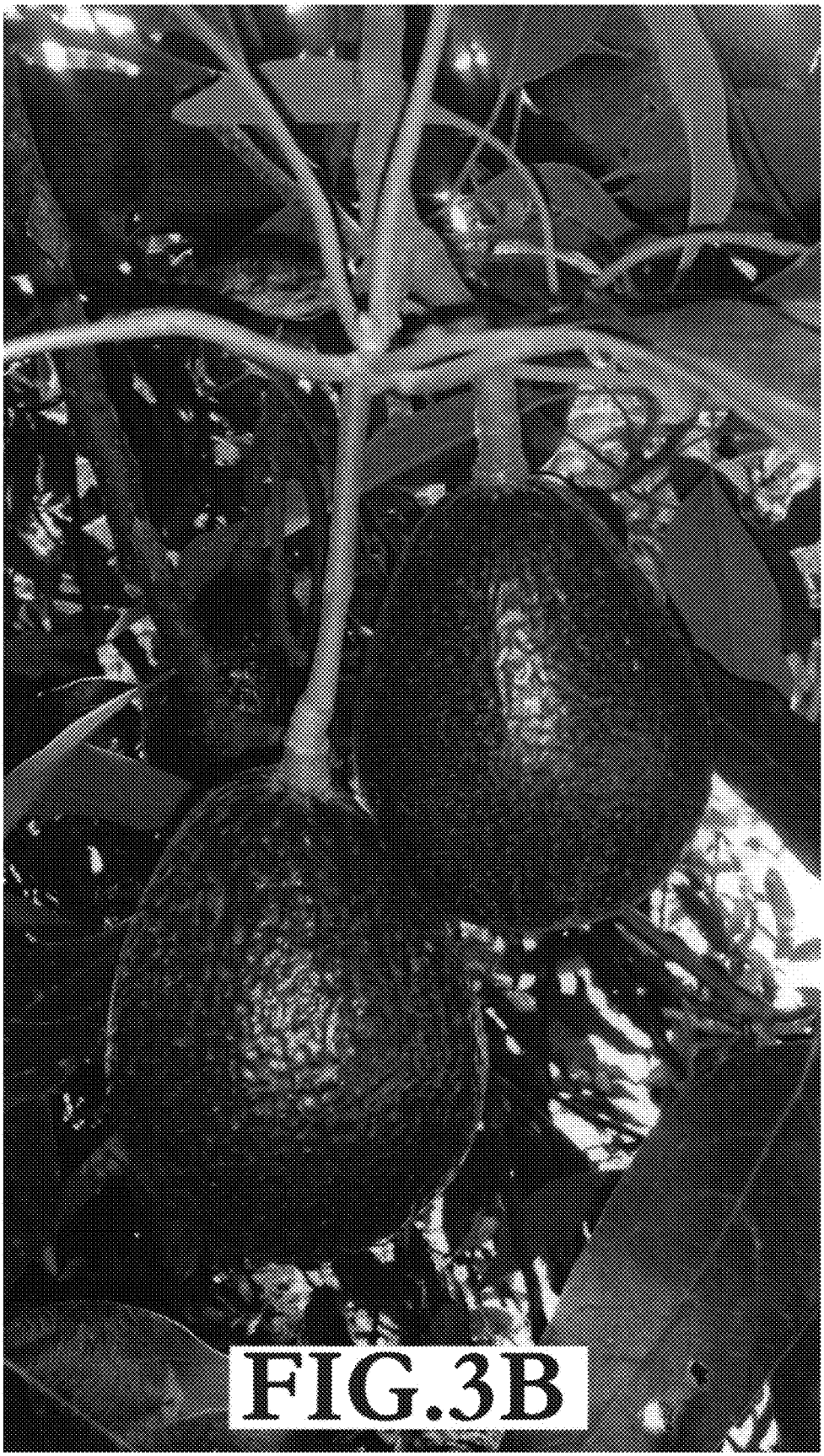
Figure 4:
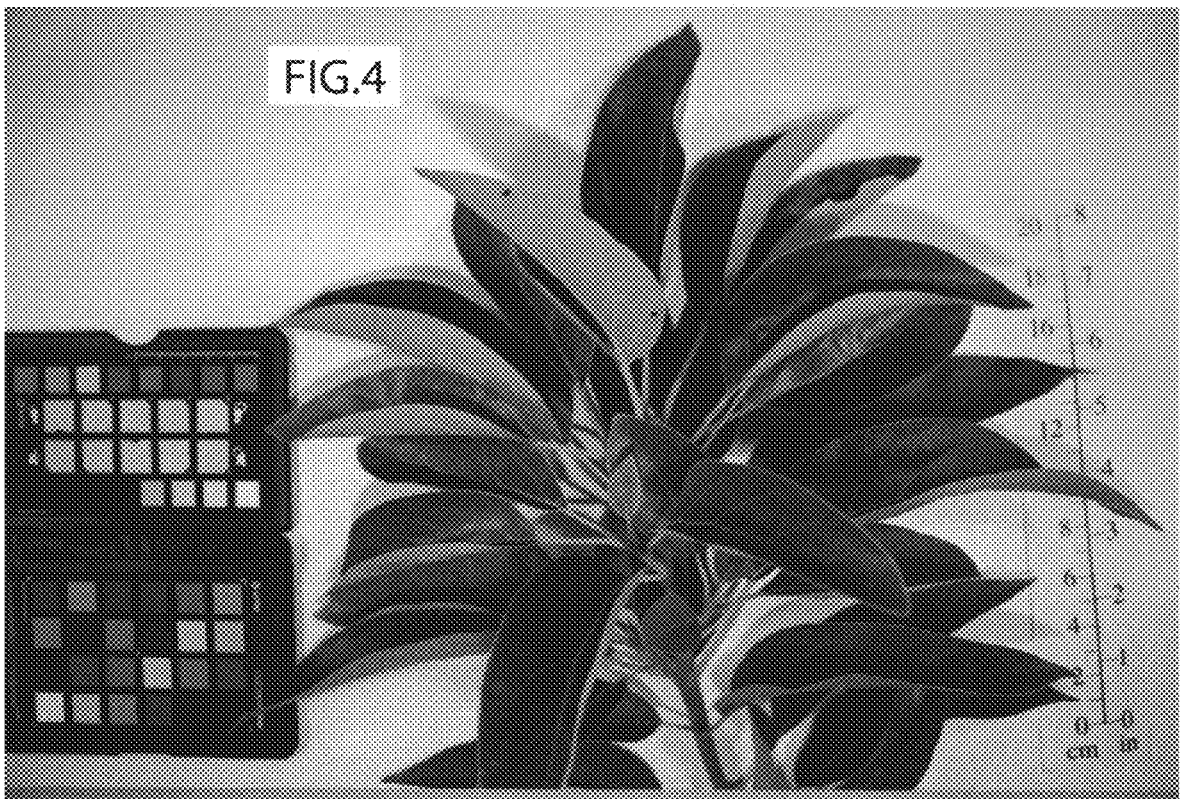
FIG. 4 illustrates typical vegetative flush and young/mature shoots of 'BL 5-552' as collected during the summer of 2017 in Irvine, Calif.
Figure 5:
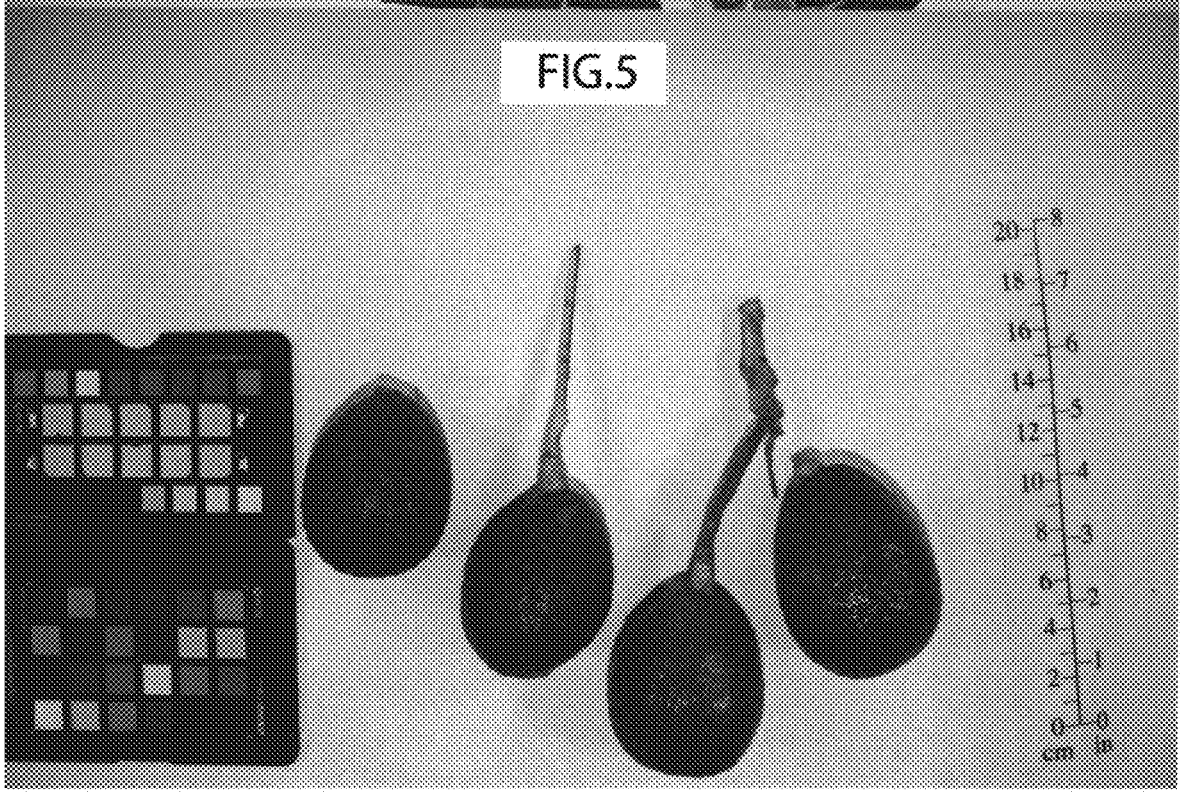
FIG. 5 illustrates typical immature fruit of 'BL 5-552' and their accompanying pedicels and shoots as collected during the summer of 2017 in Irvine, Calif.

The following is a detailed description of the new 'BL 5-552' variety. Trees for this description were grown at experimental orchards in Irvine, Calif., and Riverside, Calif. These trees were approximately 17 to 30 years of age, and had been grafted on *Persea americana* seedling understock. Additional tree, fruit and flower data were obtained from trees grown in Limpopo Province, South Africa. These trees were roughly 2-15 years of age. When reference to other varieties appears for comparative purposes, where possible, such varieties were approximately of equivalent age. Color chart information is with reference to The R.H.S. Colour Chart of The Royal Horticultural Society, London, England, 2001, $4^{th}$ Ed.

Tree:

*Growth habit*.—'BL 5-552' is open, spreading growth habit with no drooping branches, very similar to the 'N4(-)5' variety. This can be compared to an upright habit with semi drooping branches for the 'Gwen' and 'Lamb/Hass' varieties. Internode lengths on the shoot are, on average, 33.8 mm in length.

*Height*.—Generally equivalent to the 'Lamb/Hass' variety, which is 4.3 m tall in Irvine, Calif.

*Width*.—Generally equivalent to the 'Lamb/Hass' variety. which is 3.6 m wide in Irvine, Calif.

Main stem:

*Bark*.—Substantially identical to that of the 'Hass', 'Gwen', 'N4(-)5', and '3-29-5' varieties. The new wood is smooth without corky lenticels. The old wood is corky in appearance as most other avocado varieties and light brown or gray, RHS Greyed-Green 197C, in coloration.

*Trunk size*.—Approximately 57.5 cm in circumference on average. This can be compared to an average circumference of 67.1 cm for the 'N4(-)5' variety and 56.1 cm for the 'Reed' variety.

Branch:

*Color*.—The color of the one year old branch is RHS Yellow Green N144A, the most recent fully formed flush is also RHS Yellow Green N144A.

*Smoothness*.—The bark of a one year old branch is smooth.

Young shoot (flush):

*Intensity of anthocyanin coloration*.—Moderate, RHS Grey Brown N199B, underside is RHS Yellow Green 147C. Young leaf surface is moderately glossy.

*Young shoot color of lenticels*.—Not very conspicuous: Yellow to light green in color, generally RHS Yellow Green 144A.

*Young leaf color of pubescence of petiole*.—White.

*Lenticels*.—The lenticels of a one year old branch are not conspicuous or distinguishable, while the lenticels of the most recent fully formed flush are generally RHS Yellow Green 144A.

Mature leaf:

*Shape*.—Generally lanceolate to occasionally oval with an acute tip and an acute base. The shape is substantially the same as that of 'Lamb Hass' variety but longer and more narrow than the 'BL 516' variety or more oblong lanceolate to lanceolate for the 'Gwen' variety. Leaf base is acute and leaf apex is mostly acute which is substantially similar to 'Gwen' and 'Harvest'. This can be compared to the 'Hass' or '3-29-5' varieties, which have a more intermediate to acute apex. The leaf blade of 'BL 5-552' does not twist along its entire length, nor does the apex of the leaf exhibit twisting.

*Bearing*.—Alternate.

*Attitude*.—Upwards attitude of leaf to branch, which is much the same as for 'N4(-)5' variety. This can be compared to the outwards and upwards attitude of leaf to branch, for the 'Lamb/Hass' and 'BL 516' varieties or an upwards and outwards attitude for 'Gwen' variety.

*Length*.—Approximately 14.9 cm on average. This can be compared to 19.9 cm for 'Gwen' and 'Hass' varieties, 15.3 cm for the '3-29-5' variety, 18.2 cm for the 'BL 516' variety, and 20.0 cm for the 'N4(-)5' variety on average.

*Width*.—Approximately 5.7 cm on average. This is comparable to the can be compared to 6.7 cm for the 'Gwen' variety, 6.9 cm for the 'BL 516' variety, 7.8 cm for the 'Hass' and 'N4(-)5' varieties, and 6.4 cm for the '3-29-5' variety on average.

*Leaf weight*.—Approximately 1.78 g on average. This can be compared to approximately 3.95 g for the 'Hass' variety, 2.05 g for the '3-29-5' variety, 2.65 g for the 'N4(-)5' variety, 2.30 g for the 'Gwen' variety and 2.78 g for the 'BL 516' variety on average.

*Color*.—Near RHS Green 137A on the upper surface and near RHS Green 138B on the under surface.

*Texture*.—Somewhat pubescent and leathery when young and leathery when mature.

*Venation*.—Pinnate and near RHS Yellow-Green 145A in color. Venation on upper surface is level with the rest of leaf surface.

*Margin*.—Entire. Leaf undulation is very weak to non-existent.

*Petiole*.—Commonly 35.6 mm in length, and approximately 2.0 mm in diameter. Color of petiole is RHS Yellow-Green 145A.

*Anise aroma*.—Very faint to absent and comparable to leaves of the 'N4(-)5' variety.

Flower:

*Bud size*.—Approximately 7.2 mm in length and 3.2 mm in diameter.

*Bud shape*.—Ovate/oval initially, progressing to oval/lanceolate.

*Bud color*.—RHS Yellow-Green 149C or RHS Yellow-Green 149B.

*Opening*.—Belongs to group "B", Opens as female in the afternoon of the first day and closes in the evening or early night to open as male the morning of the second day. Accordingly, it can be interplanted with complementary flower types to possibly boost fruit set and yield by making pollen available at the appropriate time. Bees (e.g. European honey bees) can be used to advantage as pollinators.

*Tepals*.—Borne in two whorls of three perianth lobes. The tepals are intact, pubescent and possess margins that are not wavy or undulating. The tepal coloration (upper and lower surfaces) is near RHS Yellow-Green Group 149C.

*Stamen*.—There commonly are nine fertile stamens with each having four pollen chambers, two basal orange nectar glands, and three staminoidia. The anthers are tetrathecal.

*Pistil*.—The single pistil has one carpal with one ovule. The ovary is superior.

*Pedicel*.—Commonly approximately 3.4 mm in length and approximately 0.9 mm in diameter. The coloration is near RHS Yellow-Green Group 150C.

*Number of flowers on infloresence*.—Approximately 146 flowers per inflorescence, with approximately 9 flowers per secondary infloresence axis. Secondary inflorescence axis has an average length of 84 mm.

*Fragrance*.—Absent.

*Bloom*.—Bloom period in Irvine, Calif. varies with cultural conditions. On average 'BL 5-552' has been found to bloom from February through May.

FRUIT, FRUIT AND PRODUCTION CHARACTERISTICS

Fruit:

*Length*.—Approximately 110.8 mm on average.

*Diameter*.—Approximately 88.7 mm on average.

*Weight*.—Approximately 276.6 gms on average. This is larger than the 'Hass', the '3-29-5' and the 'Lamb/Hass' varieties which averaged 206.9 gms, 255.4 gms and 274.2 gms respectively.

*Shape*.—Generally rhomboidal, or occasionally, obovate or high spheroid shaped w/fruit apex being very slightly asymmetric in position with a rounded shape and fruit base being very slightly depressed to somewhat flattened. Compare this to the 'Hass' variety which varies from ellipsoid to obovate, the 'Gwen' and 'N4(-)5' varieties which are generally an inverted high spheroid, and the '3-29-5' variety which is generally inverted high spheroid.

*Color of peduncle*.—RHS Yellow-Green N144A.

*Color of skin*.—Mature, hard fruit is generally RHS Green Group 135A in coloration. Mature, soft fruit varies in a range including RHS Green 139A, RHS Yellow-Green 147A, and RHS Green 137A. Immature, hard fruit varies in a range including RHS Green Group141A, and RHS Green Group 141B. Lenticels are RHS Yellow-Green N144A in color and are only distinct from background RHS Yellow-Green N144A color approaching stylar end, unlike in the 'BL 516' and '3-29-5' varieties which have distinct lenticels throughout the fruit's skin surface.

*Texture of skin*.—Slightly pebbled.

*Presence of longitudinal ridges*.—Absent.

*Thickness of skin*.—Somewhat leathery in consistency, not corky or membranous. Width averages 1.7 mm as compared to 1.6 mm for 'Hass' variety, 1.8 mm for '3-29-5' variety, 1.2 mm for 'BL 516' variety and 1.5 mm for 'Lamb/Hass' variety.

*Adherence of skin to flesh*.—Minimal.

*Main color of flesh*.—RHS Yellow Group 4C and RHS Yellow Green Group N135A near the skin.

*Width of intensely colored area next to the skin*.—Approximately 2.5 mm.

*Conspicuousness of fibers in flesh*.—Inconspicuous.

*Fruit pedicel*.—Approximately 10.1 mm in diameter. Pedicel color is RHS Yellow Green 144A and generally has a wrinkled surface.

*Time of harvesting*.—'BL 5-552' typically ripens later than 'Hass' variety and is a summer and fall fruit (in Irvine, Calif.).

Seed:

*Length*.—Approximately 4.6 cm on average.

*Width*.—Approximately 4.4 cm on average.

*Weight*.—Approximately 38.9 gms on average. This is smaller than '3-29-5', and 'Lamb/Hass' varieties measured, which averaged 40.5 gms, and 39.5 gms respectively and larger than 'Hass', which averaged 30.6 gms.

*Shape* (*in longitudinal section*).—Base flattened, apex conical shape as compared to the 'N4(-)5' and 'Gwen' varieties which are spheroid, the 'Hass' variety which is variable but mostly ellipsoid, or the '3-29-5' variety which is broadly obovate.

*Shape* (*in cross section*).—Generally circular.

*Color of seed coat* (*fresh*).—Greyed Orange Group 164B.

*Cotyledon color*.—Orange White 159A.

Productivity: Generally favorable to that of the 'Fuerte' variety, and likely with less inconsistency in annual yields to the 'Fuerte' variety.

Hardiness: Generally comparable to other commercial varieties such as the 'Hass', 'N4(-)5', '3-29-5' and 'Lamb/Hass' varieties. 'BL 5-552' is hardy in the United States Department of Agriculture (USDA) plant hardiness zones 9b, 10a, 10b.

Market use: 'BL 5-552' is a superior tasting avocado that could, in some countries, compete favorably with the 'Fuerte' and 'Ryan' varieties for both fresh retail and food service markets. Also, the fruit can serve as a source for processed guacamole and other avocado by-products. The tree shows more consistent yield of good quality, easy peeling green skinned fruit than the 'Fuerte' commercial variety, and its fruit is also less susceptible to bruising and fungal diseases than the fruit of the 'Fuerte' variety. The 'BL 5-552' fruit is also of higher eating quality than 'Ryan' fruit and has a smaller seed to flesh ratio than the 'Ryan' variety.

What is claimed is:

1. A new and distinct rootstock variety of avocado tree having the characteristics substantially as described and illustrated herein.

* * * * *